United States Patent
Bassin

(10) Patent No.: US 10,300,232 B2
(45) Date of Patent: *May 28, 2019

(54) METHODS AND APPARATUS FOR VARYING THE BACK-UP RATE FOR A VENTILATOR

(71) Applicant: ResMed Limited, Bella Vista (AU)

(72) Inventor: David John Bassin, Sydney (AU)

(73) Assignee: ResMed Limited (AU)

( * ) Notice: Subject to any disclaimer, the term of this patent is extended or adjusted under 35 U.S.C. 154(b) by 114 days.

This patent is subject to a terminal disclaimer.

(21) Appl. No.: 15/157,527

(22) Filed: May 18, 2016

(65) Prior Publication Data

US 2016/0256645 A1 Sep. 8, 2016

Related U.S. Application Data

(63) Continuation of application No. 14/662,394, filed on Mar. 19, 2015, now Pat. No. 9,364,627, which is a (Continued)

(30) Foreign Application Priority Data

Mar. 7, 2003 (AU) .................................. 2003901042

(51) Int. Cl.
  *A61M 16/00* (2006.01)
  *A61M 16/04* (2006.01)
  (Continued)

(52) U.S. Cl.
  CPC ........ *A61M 16/0069* (2014.02); *A61M 16/00* (2013.01); *A61M 16/0003* (2014.02);
  (Continued)

(58) Field of Classification Search
  CPC .. A61M 16/0066; A61M 16/00; A61M 16/04; A61M 16/06; A61M 16/0875;
  (Continued)

(56) References Cited

U.S. PATENT DOCUMENTS 5,107,831 A    4/1992  Halpern et al.
5,490,502 A    2/1996  Rapoport et al.
              (Continued)

FOREIGN PATENT DOCUMENTS

AU    24896/01 A    9/2001
EP    0324275 A1    7/1989
              (Continued)

OTHER PUBLICATIONS

Baoguo, Wang, "Practical Therapeutics by ventilator", published by People's Medical Publishing House, first version printed on Mar. 1, 1994.

(Continued)

*Primary Examiner* — Steven O Douglas
(74) *Attorney, Agent, or Firm* — Botos Churchill IP Law LLP

(57) ABSTRACT

A ventilator device delivers ventilatory support to a patient in a back up timed mode when patient respiration is not detected or a spontaneous mode when patient respiration is detected. The timing threshold governing the back-up mode is chosen to deviate from normal expected respiration time for the patient to promote patient initiated ventilation in the spontaneous mode but permit back-up ventilation in the event of apnea. Automated adjustments to the timing threshold during the timed mode are made from the less vigilant timing threshold to a more vigilant threshold at or near a timing of normal expected breathing of the patient. Such adjustments may be made from a minimum to a maximum vigilance timing settings or incrementally there between as a function of time in the timed mode which is preferably the number of delivered machine breaths.

15 Claims, 4 Drawing Sheets

Related U.S. Application Data continuation of application No. 13/870,501, filed on Apr. 25, 2013, now Pat. No. 9,050,429, which is a continuation of application No. 13/242,752, filed on Sep. 23, 2011, now Pat. No. 8,448,640, which is a continuation of application No. 12/573,382, filed on Oct. 5, 2009, now Pat. No. 8,051,852, which is a continuation of application No. 11/778,895, filed on Jul. 17, 2007, now Pat. No. 7,628,151, which is a continuation of application No. 10/794,501, filed on Mar. 5, 2004, now Pat. No. 7,255,103.

(51) Int. Cl.
*A61M 16/06* (2006.01)
*A61M 16/08* (2006.01)
*A61M 16/20* (2006.01)

(52) U.S. Cl.
CPC ...... *A61M 16/0066* (2013.01); *A61M 16/024* (2017.08); *A61M 16/04* (2013.01); *A61M 16/06* (2013.01); *A61M 16/0875* (2013.01); *A61M 16/20* (2013.01); *A61M 2205/3334* (2013.01); *A61M 2205/50* (2013.01); *A61M 2205/502* (2013.01); *A61M 2230/005* (2013.01); *A61M 2230/40* (2013.01)

(58) Field of Classification Search
CPC .......... A61M 16/0069; A61M 16/0003; A61M 16/20; A61M 16/024; A61M 2205/3334; A61M 2205/50; A61M 2205/502; A61M 2230/005; A61M 2230/40
USPC ............. 128/204.18, 204.21, 204.23, 204.26
See application file for complete search history.

(56) References Cited

U.S. PATENT DOCUMENTS

| | | |
|---|---|---|
| 6,213,119 B1 | 4/2001 | Brydon et al. |
| 6,484,719 B1 | 11/2002 | Berthon-Jones |
| 6,532,960 B1 | 3/2003 | Yurko |
| 6,644,312 B2 | 11/2003 | Berthon-Jones et al. |
| 7,255,103 B2 | 8/2007 | Bassin |
| 7,628,151 B2 | 12/2009 | Bassin |
| 8,051,852 B2 | 11/2011 | Bassin |

FOREIGN PATENT DOCUMENTS

| | | |
|---|---|---|
| EP | 1346743 A1 | 9/2003 |
| JP | 2002-516159 A | 6/2002 |
| WO | 97/15343 A1 | 5/1997 |
| WO | 99/61088 A1 | 12/1999 |
| WO | 02/26283 A2 | 4/2002 |
| WO | 02/094358 A1 | 11/2002 |
| WO | 03008027 A1 | 1/2003 |

OTHER PUBLICATIONS

Extended European Search Report for Application No. EP11180545 dated Nov. 21, 2013.
International Search Report and Written Opinion for Application No. PCT/AU2004/000272 dated Apr. 22, 2004.
Request Form for Invalidation for Chinese Application 200910173495.7 dated May 1, 2013.
Supplemental Search Report, EP Application No. 04717523.7, European Patent Office, dated Nov. 5, 2010. cited by other.
The Decision for Invalidation for Chinese Application 200910173495.7 dated Sep. 26, 2014.

METHODS AND APPARATUS FOR VARYING THE BACK-UP RATE FOR A VENTILATOR

CROSS-REFERENCE TO RELATED APPLICATIONS

The present application is a continuation of U.S. patent application Ser. No. 14/662,394, filed Mar. 19, 2015, now U.S. Pat. No. 9,364,627, which is a continuation of U.S. patent application Ser. No. 13/870,501, filed Apr. 25, 2013, now U.S. Pat. No. 9,050,429, which is a continuation of U.S. patent application Ser. No. 13/242,752, filed Sep. 23, 2011, now U.S. Pat. No. 8,448,640, which is a continuation of U.S. patent application Ser. No. 12/573,382, filed Oct. 5, 2009, now U.S. Pat. No. 8,051,852, which is a continuation of U.S. patent application Ser. No. 11/778,895, filed Jul. 17, 2007, now U.S. Pat. No. 7,628,151, which is a continuation of U.S. patent application Ser. No. 10/794,501, filed Mar. 5, 2004, now U.S. Pat. No. 7,255,103, which claims priority from AU 2003901042, filed Mar. 7, 2003, the disclosures of which are hereby incorporated herein by reference.

FIELD OF THE INVENTION

The invention relates to the field of automatically controlled mechanical ventilators for use in treating respiratory disorders such as respiratory insufficiency. In particular, the invention relates to a method and apparatus providing a more appropriate back-up rate for ventilation when patients are not breathing spontaneously.

BACKGROUND OF THE INVENTION

Both positive and negative pressure mechanical ventilators have been used for decades to treat patients with respiratory disorders. A range of ventilators are described in "Principles & Practice of Mechanical Ventilation", Edited by M J Tobin (1994, McGrawHill Book Company, ISBN 0-07-064943-X). Other ventilators are described in "Respiratory Therapy Equipment", by S. P. McPherson (3rd Ed., 1985, C. V. Mosby Company, ISBN 0-8016-3312-5). Other ventilators are described in "Automatic Ventilation of the Lungs" by Mushin et al (3rd Ed, 1980, Blackwell Scientific Publications, ISBN 0-632-002286-7).

Positive pressure ventilators provide a supply of air or breathable gas at positive pressure to a patient's airway. Flow is volume of air per unit time. Tidal volume is the volume of air entering and leaving the lungs during the respiratory cycle. Minute ventilation is the volume of air delivered to a patient in 1 minute. There are two general approaches to control of ventilators: (1) volume or flow; and (2) pressure control. A ventilator may be programmed to control the volume of air delivered to a patient by adjusting the minute ventilation. The rate at which the air is delivered to the patient is breaths (or cycles) per unit time.

In order to achieve the desired minute ventilation, both the rate and volume of air delivered to a patient can be varied.

In this specification, a ventilator will be said to be triggered into an inspiratory phase and cycled into an expiratory phase. Spontaneous breaths are those that are initiated by the patient. If the ventilator determines either the start or end of inspiration, then the breath is considered mandatory. If the patient triggers the ventilator (e.g., with a spontaneous breath), the ventilator is said to be an assistor. If time triggers the ventilator into the inspiratory phase, the ventilator is said to be a controller. If the patient can assist and the machine can back him up (if his breathing rate drops or stops altogether), the ventilator is designated an assistor/controller. It is possible for a machine to be all three.

It is:
(1) an assistor when it is patient-triggered and there is no timed backup rate;
(2) a controller when it is time-triggered and no assist mechanism is provided; or
(3) an assistor/controller when the timed rate backs up the patient's rate (sometimes called "spontaneous/timed").

When the ventilator switches between inspiratory and expiratory modes at the same time as the spontaneously breathing patient, the ventilator is said to be in synchrony with the patient. Loss of synchrony can lead to patient discomfort and ineffective ventilation. For purposes of this description, a spontaneous/timed ventilator is considered to be in a spontaneous mode when it is delivering ventilation support in response to detected patient respiration. Similarly, the spontaneous/timed ventilator is considered to be in a timed mode when it is delivering a machine breath according to a back up timing threshold back up rate in response to a failure to detect patient respiration.

A method for providing ventilatory assistance in a spontaneously breathing subject is described in U.S. Pat. No. 6,484,719 (Berthon-Jones), the contents of which are hereby incorporated by cross-reference.

In some situations, a spontaneous/timed ventilator can fail to detect when the patient switches between inspiration and expiration. Therefore some ventilators have a "time-out" for a spontaneous mode. Such ventilators will switch from the spontaneous mode (waiting for the patient) to a timed mode (delivering ventilation at the back up rate} at the end of the time-out period. An improved system for a "time-out" is described in U.S. Pat. No. 6,213,119, the contents of which are hereby incorporated by cross-reference.

As discussed herein, the back-up rate (cycles/time) may be alternatively described by its reciprocal, the back-up period (time/cycle).

In programming an automatic ventilator, the problem arises as to the choice of the most appropriate back-up rate for the device.

BRIEF SUMMARY OF THE INVENTION

In accordance with a first aspect of the invention, a ventilator is designed with a back-up process or back up timing module such that it is configured or programmed to deliver timed breaths with a timing threshold or back-up rate in the event a spontaneous breath is not detected. The timing threshold or back up rate may, in a first embodiment, be set to a first rate that is substantially lower (i.e., less frequent) than the patient's normal respiratory rate. In this regard it is chosen to depart or deviate from that which would ordinarily be associated with normal or expected patient respiration in a manner that promotes patient initiated ventilation by the ventilator but allows timed ventilation in the event of apnea. Accordingly, the first rate is set substantially lower so that the ventilator will less likely interfere with the patient's normal breathing cycle, meaning that the chances for the ventilator to resume a spontaneous mode from a timed mode or continue within spontaneous mode are increased when the instantaneous backup rate is lower than the backup rate which would have been set with a conventional fixed backup rate ventilator. In other words, if the patient again commences spontaneous breathing, the timed mode is discontinued or the spontaneous breathing mode continues. If the patient continues to require timed ventilation in the absence of detected breathing, meaning that spontaneous breathing has not re-commenced, the ventilator will automatically normalize the timing threshold to a more vigilant timing or an approximately normal expected respiratory timing. Thus, the ventilator gradually or step-wise increases the breathing rate from the first rate to a second rate which is at, closer to, or slightly lower than the patient's normal breathing rate. Of course, the second rate may also change to be higher than the patient's normal breathing rate, depending on the particular application.

In other words, a low timed rate is used to decrease the likelihood of false entry into the timed mode of the ventilator yet the timing rate is adjustable in the timed mode to permit appropriate ventilation of a patient during the timed mode. Thus, the back-up rate is automatically adjusted as a function of elapsed time in the timed mode, increasing towards the patient usual or average respiratory rate. In terms of a timing threshold that is a back-up period, the back-up period is automatically adjusted as a function of the time in the timed mode, decreasing towards the patient's usual or average respiratory period.

In another aspect, the timed rate may be adjustable between two limits, namely, a first lower rate and a second rate, higher than the first. In one form, the first rate is significantly lower than the patient's usual respiratory rate and the second rate is at or slightly lower than the patient's usual respiratory rate. Of course, the second higher rate may optionally be at or higher than the patient's usual or average respiratory rate. When the ventilator switches to the timed mode, having failed to detect a spontaneous breath, the ventilator is initially set to the first lower rate and then the patient is ventilated. If after a predetermined period, a spontaneous patient breath still has not been detected by the ventilator, the back-up rate is increased towards the second rate. In one preferred form, apparatus in accordance with the invention changes the back-up rate from the lower rate to the faster rate over approximately 5 breaths within the timed mode if spontaneous breaths are not detected.

In one form, in apparatus in accordance with the invention, the second rate is approximately 25% faster than the first rate. In another preferred form, the second rate is approximately 50% faster than the first rate.

In another embodiment, the adjustable back-up rate is automatically modified as a function of adequacy of ventilation. In a preferred embodiment of such an adjusting back-up rate, ventilation adequacy affects the rate of change of the adjustments to the back-up rate between its minimum and maximum values.

In one embodiment, within the timed mode the device periodically returns the timing threshold to a less vigilant timing threshold to promote resynchronization with the patient.

Other aspects of the invention are described in the detailed description herein.

DETAILED DESCRIPTION

Figure 1:
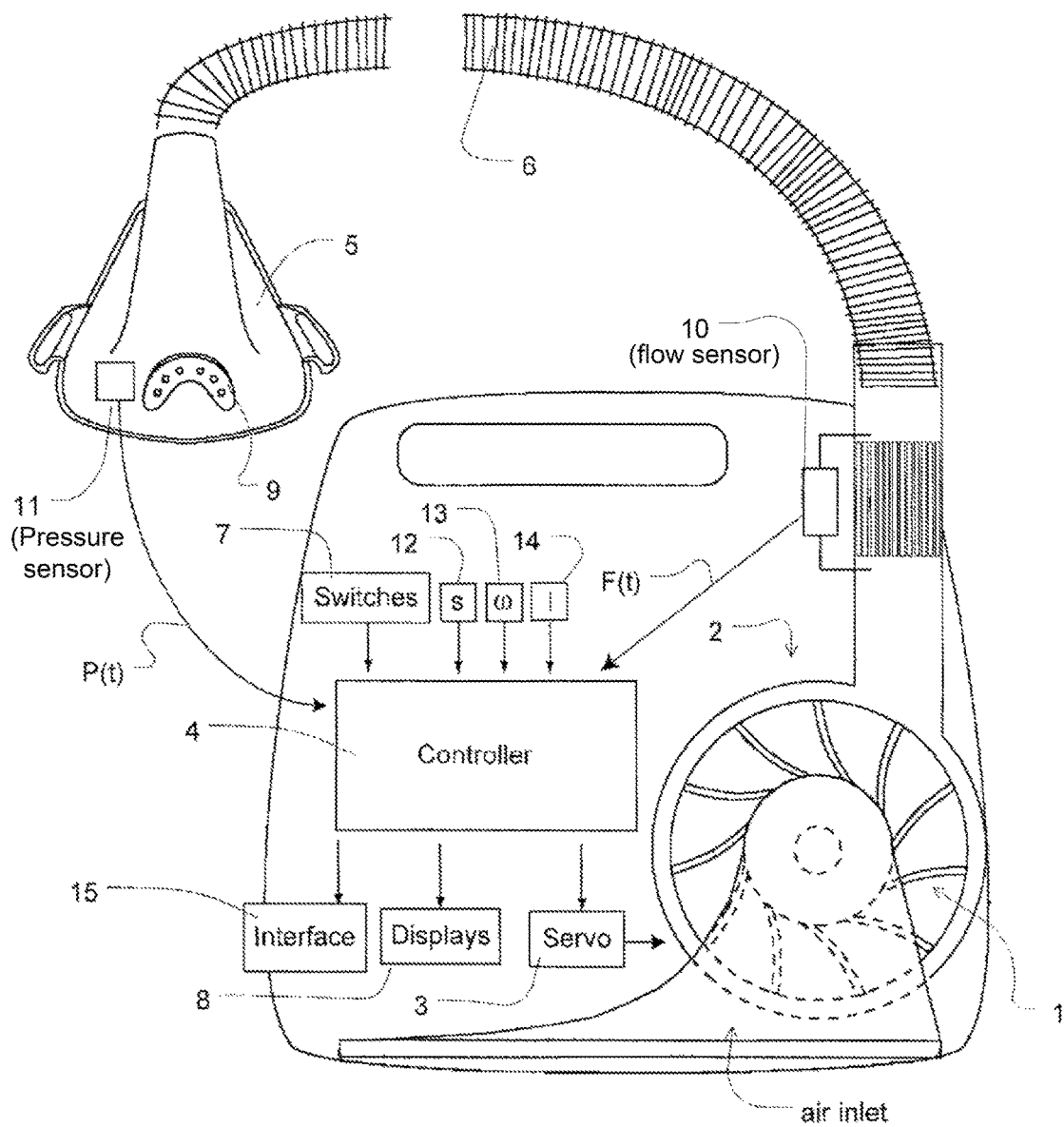
FIG. 1 shows a ventilator programmed in accordance with an embodiment of the invention.

FIG. 1 shows, by way of example, apparatus suitable for performing the invention. FIG. 1 shows an impeller 1 connected to an electric motor 2 under the control of a servo-controller 3 which is in turn under the control of a controller 4. In one form the controller 4 is a microprocessor based controller, such as an Intel '486 microprocessor. The impeller 1 and motor 2 form a blower. Air from the blower passes along a flexible conduit 6 to a patient interface such as a nasal mask 5 with a vent 9. While a nasal mask is illustrated, the invention may be used in conjunction with a nose-and-mouth mask, full face mask or endotracheal tube. A number of switches 7 are connected to the controller. A number of sensors are connected to the controller, namely: flow 10, pressure 11, snore 12, motor speed 13 and motor current 14. There are a set of displays 8 connected to the controller 4 for displaying information from the controller. There is an interface 15 to enable the controller 4 to communicate with an external device such as a computer. With such a device, changes in the speed of the blower may be controlled to alternatively change the pressure in the mask to implement ventilatory support. Optionally, the blower motor speed may be held generally constant and pressure changes in the mask may be implemented by controlling an opening of a servo-valve (not shown) that may variably divert/vent or deliver airflow to the mask. Those skilled in the art will recognize other devices for generating ventilatory support and delivering same to a patient.

The controller 4 or processor is configured and adapted to implement the methodology described herein and may include integrated chips, a memory and/or other instruction or data storage medium. For example, programmed instructions with the control methodology may be coded on integrated chips in the memory of the device or such instructions may be loaded as software. With such a controller, the apparatus can be used for many different pressure ventilation therapies simply by adjusting the pressure delivery equation that is used to set the speed of the blower or to manipulate the venting with the release valve. Those skilled in the art will also recognize that aspects of the controller may also be implemented by analog devices or other electrical circuits.

Figure 2:
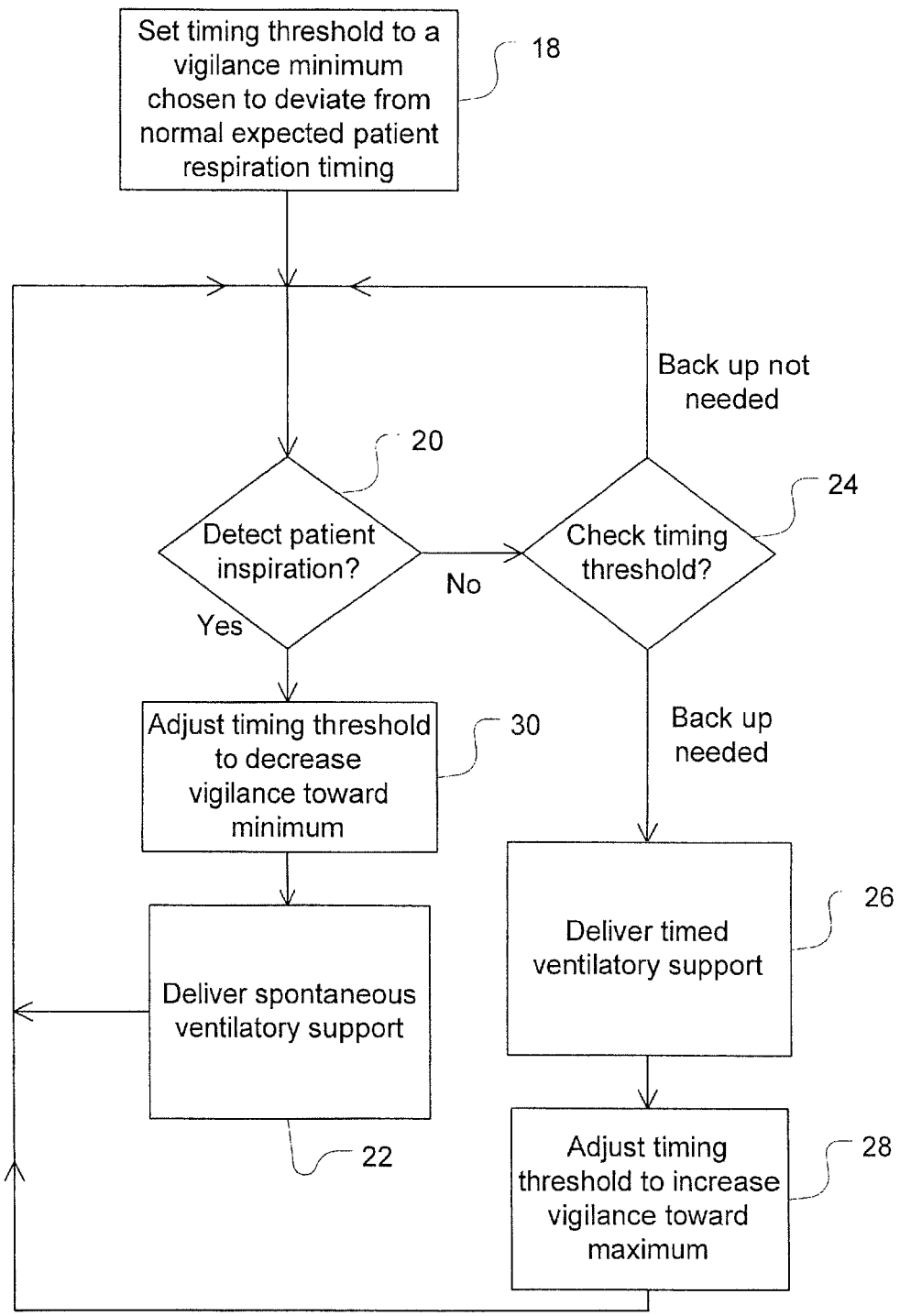
FIG. 2 is a flow chart of one embodiment of steps taken in the automatic adjustment of a timing threshold.

Generally speaking, as illustrated by the step of the flowchart of FIG. 2, a device in accordance with the invention can deliver ventilatory support in a spontaneous mode (step 22) to synchronously ventilate the patient in accordance with detecting the patient's inspiration (step 20). However, if the patient inspiration is not detected before the lapsing of some timing threshold (e.g., a timing rate ($1/T_{current}$) or timing period ($T_{current}$) determined by comparison of the threshold by a measured rate or period (step 24), the device will initiate a timed mode (step 26) in which a machine initiated breath will be delivered. Those skilled in the art will recognize methods for entering the timed mode by enforcing a timing threshold. Automated adjustments to the timing threshold, ($1/T_{current}$ or $T_{current}$) may then be implemented in steps 28 and 30 as described further herein.

In the following description, "period" means the reciprocal of rate unless otherwise indicated. Define $T_{apn}$ to be a desired time for the backup period while the patient is not breathing or the desired time from the start of an inspiratory breath (non-patient triggered) to the time for the start of a subsequent inspiratory breath (non-patient triggered), namely the reciprocal of the rate desired when the patient is not triggering the ventilator and is at least apparently, if not actually apnoeic, from the point of view of the ventilator. Preferably this rate is approximately that of the normal expected respiratory rate for the patient but it may be higher or lower as desired. Define $T_{spont}$ to be the desired time for the backup period while the patient is spontaneously breathing which is preferably chosen to deviate from the normal expected respiratory rate of the patient such that the timing threshold is less vigilant than normal breathing. Define $T_{current}$ to be a current backup period being applied to control the delivery of ventilation to the patient.

If the current breath started at time $t_{breathstart}$ then a machine initiated or "timed" breath will occur at $t_{breathstart}+T_{current}$ if the patient has not triggered the ventilator before this time. It is to be understood that $T_{spont}$ and $T_{apn}$ are chosen so that with the respiratory mechanics of the Patient being treated, a decrease in respiratory period from $T_{spont}$ to $T_{apn}$ with fixed pressure support levels, results in a monotonic increase in ventilation. Those skilled in the art will recognize various methods for determining the time of recurring respiratory event $t_{breathstart}$ or otherwise detecting an event in the respiratory cycle for purposes of timing the delivery of spontaneous or timed cyclical ventilation support.

(I) Basic Methodology $T_{current}$ is initialized to $T_{spont}$. If a timed breath occurs, Tcurrent is decremented by some amount $\Delta_d T_{current}$ (not necessarily a constant) and the result is then limited to be at least $T_{apn}$. More specifically, in one implementation, $T_{current}$ is decremented by $(T_{spont}-T_{apn})/N_{dec}$, where $N_{dec}$ is, for example, 5, so that in this case after 5 timed breaths the apnoeic backup rate is reached. This adjustment to the timing threshold is illustrated in step 28 of FIG. 2.

Generally $N_{dec}$ should not be too small (e.g., 1) because one wants to maximize the chances of resynchronising with the patient. The longer the period of time during which the patient has not triggered the ventilator, the less likely it is that triggering will occur in the immediate future, and the more likely it is that hypoxia will occur if timed ventilation continues at a low rate.

If a triggered breath occurs at any time, $T_{current}$ is incremented by some amount $\Delta_i T_{current}$, and the result is then limited so that it is at most $T_{spont}$. More specifically, in one implementation, $T_{current}$ is incremented by $(T_{spont}-T_{apn})N_{inc}$, where in the preferred implementation $N_{inc}=1$, so that in this case after 1 triggered breath the backup rate returns immediately to the spontaneous breathing backup rate $T_{spont}$. It is desirable that $N_{inc}<N_{dec}$, because if one spontaneous breath is detected there are likely to be more, and one wants to maximize the chance of triggering on the next one. This adjustment to the timing threshold is illustrated in step 30 of FIG. 2.

Figure 3:
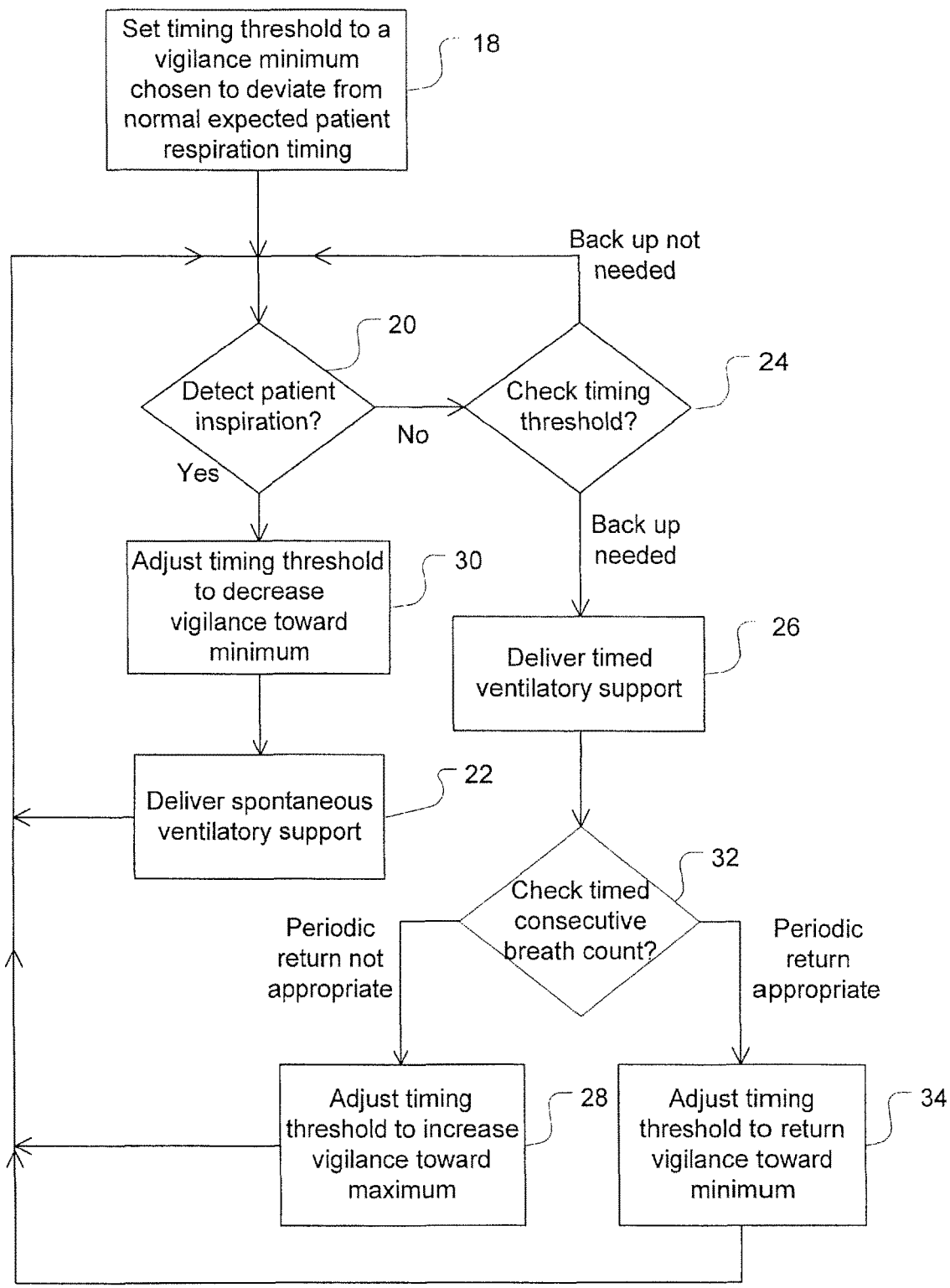
FIG. 3 is a flow chart of an alternative embodiment of steps taken in the automatic adjustment of a timing threshold.
Figure 4:
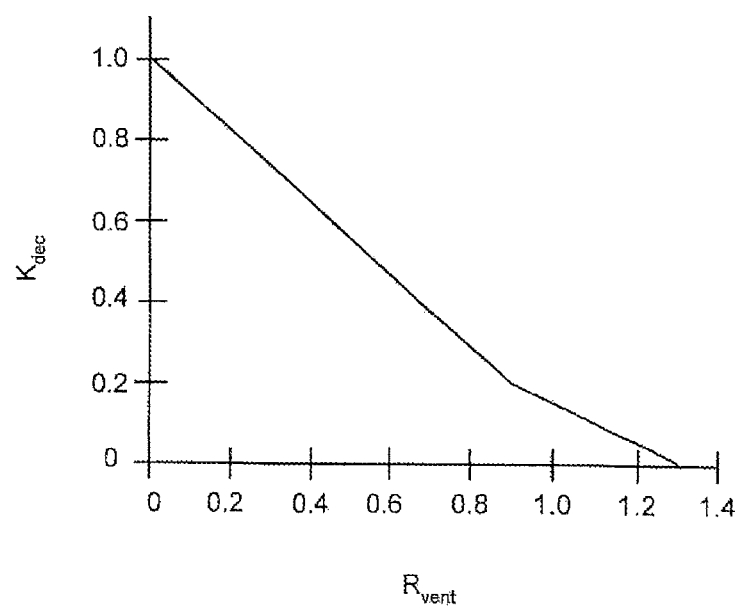
FIG. 4 shows a "delta" function for adjusting the back-up rate in accordance with the adequacy of ventilation.

In one implementation as illustrated by FIG. 3, when successive timed breaths are delivered with a period of $T_{apn}$ occasional breaths (for example, 1 breath in each contiguous series of 10 timed breaths) are delivered with a longer period, up to $T_{spont}$ in order to increase the chance of resynchronizing with the patient, while on average ventilating the patient at a rate close to the reciprocal of $T_{apn}$. Thus, while the ventilator is in the timed mode, the back-up rate may be periodically modified or relaxed to be less vigilant for the purpose of promoting resynchronization with the patient as illustrated in step 34 of FIG. 3 if a certain number of consecutive timed breaths occur (step 32). Thus, in the timed mode the rate or period may be decreased or increased respectively for a breath cycle. For the following breath cycle the back-up rate is returned to a more vigilant rate or period (e.g., the patient normal expected or average breath rate or period) if no patient breath is detected that would trigger the spontaneous mode as a result of the more relaxed back-up rate or period. For example, in step 30 the ventilator may return $T_{current}$ to $T_{spont}$ and then repeat the methodology above for increasing back toward $T_{apn}$ or as preferred, after a single machine generated breath, the ventilator will adjust $T_{current}$ back to $T_{apn}$ in step 28.

(II) Advantages

Advantages of the invention include the ability to set a lower backup rate than usual, so as to interfere less than usual with the patient's spontaneous breathing, while setting a higher and thus more efficient rate which will prevail when the patient is genuinely or effectively apnoeic, thus allowing lower pressure support levels.

(III) Algorithm Using Measured Ventilation to Modify Back-Up Rate Variation Speed If a rapidly-responding measure of minute ventilation is available (with a response time typically of the order of 2 or 3 breaths, e.g., a 4th order Bessel lowpass filter of the absolute value of flow with a corner frequency of about 3.2/60 Hz), and there is also available a desired or target ventilation (as in a servoventilator, the typical case envisaged here, though the ventilator need not actually be servo-controlling the ventilation—some advantages still accrue without servo-control), then $\Delta_d T_{current}$ can be made to depend on some measure of the adequacy of the actual ventilation, for example, the ratio $R_{vent}$ of the measured ventilation to the target ventilation (e.g., $V_{meas}/V_{targ}$) which may be determined from a signal from a flow sensor or differential pressure transducer configured to do so. When $R_{vent}$ is significantly larger than 1, say $\geq 1.2$, then $\Delta_d T_{current}$ can be chosen to be 0, because ventilation is entirely adequate. In the case of a servoventilator with a low or zero minimum pressure support level, if all breaths are timed, $R_{vent}$ cannot stay at $\geq 1.2$ for any significant period of time, because the fact that $R_{vent}$ is more than 1 will cause the pressure support level to be reduced so that $R_{vent}\approx 1$. The situation of a timed breath occurring with $R_{vent}$ being $\geq 1.2$ may typically occur when a sigh is followed by a brief pause, and it is not desirable to decrement $T_{current}$ under these circumstances, because a spontaneous breath will probably occur very soon, and one wants to maximize the chances of synchronizing with it. In the absence of servo-control of pressure support level, $R_{vent}$ being $\geq 1.2$ indicates that more than adequate ventilation is being achieved at a low rate at the set pressure level (presumably regarded as acceptable), so there is no need to increase the rate.

When $R_{vent}$ is significantly less than 1, $\Delta_d T_{current}$ can be increased, so that, for example, if there is marked hypoventilation, $T_{current}$ may decrease from $T_{spont}$ to $T_{apn}$ in 2 breaths, because in this situation it is desirable to get to the more efficient apnoeic backup rate quite rapidly. Intermediate values of $R_{vent}$ should produce intermediate values of $T_{current}$ in a monotonic fashion but not necessarily using linear interpolation between the endpoints (i.e., $T_{spont}$ and $T_{apn}$). To derive the full benefit of this invention in the case of a servoventilator, it is essential that $\Delta_d T_{current}>0$ when $R_{vent}\approx 1$. The reason for this is that the automatic increase in pressure support in response to the fact that when $R_{vent}<1$ it may rapidly cause the hypoventilation to be corrected, i.e. $R_{vent}\approx 1$ so that if $\Delta_d T_{current}\approx 0$ when $R_{vent}\approx 1$, the backup period may never decrease, resulting in sustained ventilation of the patient at a lower than optimal rate using higher than optimal pressure. To prevent this, it is desirable that when $R_{vent}\approx 1$, $\Delta_d T_{current}\approx (T_{spont}-T_{apn})10$.

FIG. 3 illustrates a piecewise linear "delta" function for adjusting the back-up rate in accordance with the adequacy of ventilation by the following formula:

$$\Delta_d T_{current} = (T_{spont}-T_{apn})*K_{dec}(R_{vent})$$

As depicted in the figure, the x-axis shows a measure of the adequacy of ventilation $R_{vent}$. The y-axis shows the relative size of a correction factor ($K_{dec}$) to be applied to the back-up rate. For example, a value of 0.2 on the x-axis indicates a low adequacy of ventilation which is compensated by a relatively high correction factor, causing the back-up rate to be increased by a larger delta. In other embodiments of the invention, the delta function may have different shapes, e.g., linear, curved and/or combinations thereof. The delta function may also have other input parameters.

It should be noted that the combination of this algorithm with a fixed pressure level constitutes a form of servo-control of ventilation during apnea, though this is not the primary intention of this invention. Such a servo-control algorithm based on rate would require $\Delta_d T_{current}$ to be negative when the ventilation is above target.

In one form the apparatus has a learning mode as described in published Australian patent application AU 24896/01 (Berthon-Jones) entitled "Determining Suitable Ventilator Settings in Patients with Alveolar Hypoventilation During Sleep", also disclosed in U.S. Pat. No. 6,644, 312, the disclosure of which is incorporated by reference. During the learning mode, the device learns the patient's natural breathing rate. The lower back-up rate is then set as a function of the rate, preferably at approximately ⅔ or 67%, or alternatively 75%, of that rate, and the higher rate is set at the rate determined to be the patient's natural breathing rate or the average normal breathing rate determined from a period of time. Of course, the ventilator may include a function to prompt for input by a user of the higher and/or lower respiratory rates or periods as desired or necessary.

In one form the back-up rate is changed from the first rate to the second rate in a stepwise manner, by adding a "delta" to the back-up rate. The delta may be of fixed size, or it may be a function of a measure of the adequacy of the ventilation. In the following example of one embodiment of the invention, implemented in the C++ programming language, the function determining the size of a delta function is illustrated:

```
int VPAP __ST __Sync__RelVentErrT::CalcBackupPeriodDecrement( )
{
//Return decrement in ticks at HZ.
int MaxBackupDecrement = BackupPeriodWhenBreathing −
BackupPeriodApnoeic; double
RelVentErr;
if (RelativeVentilationErrGetP = NIL ||
    ! RelativeVentilationErrGetP->Get (RelVentErr)
    )
// No information available about ventilation error.
return MaxBackupDecrement/5;
//A goal is that if the ventilator is providing timed breaths and Is
// just reaching the target ventilation, we want to ensure that the
// apnoeic rate is reached reasonably quickly. We don't want to get
// stuck providing high pressure support at a low rate and meeting
// target this way.
if ( ReiVentErr >= 0.3 )
// Well over target, so don't change backup period at all. This might
// be e.g. a pause after a sigh.
    return 0;
double PropnOfMaxDecrement;
if (RelVent Err>= −0.1)
    PropnOfMaxDecrement = 0.2*(0.3 − RelVentErr)/0.4;
else
{
if (RelVentEff < −1.0)
    RelVentErr = −1.0; // should be unnecessary
PropnOfMaxDecrement = (−0.1 − RelVentErr) / 0.9;
}
return (int) (PropnOfMaxDecrement * MaxBackupDecrement + 0.5);
}
```

Although the invention has been described with reference to preferred embodiments, it is to be understood that these embodiments are merely illustrative of the application of the principles of the invention. Numerous modifications may be made therein and other arrangements may be devised without departing from the spirit and scope of the invention.

The invention claimed is:

1. An apparatus for setting back up support ventilation comprising:
   a ventilation generation device,
   a sensor for detecting spontaneous patient breathing, and
   a controller, including at least one processor, the controller coupled with the sensor and the ventilation generation device, the controller configured to control:
      a first machine initiated breath as a function of an initial timing threshold based on absence of a detection of a spontaneous breath by the controller;
      adjustment of the initial timing threshold to a modified timing threshold based on a predetermined number of machine initiated breath counts; and
      a second machine initiated breath as a function of the modified timing threshold.

2. The apparatus according to claim 1, wherein the predetermined number of machine initiated breath counts comprise a breath cycle.

3. The apparatus according to claim 2, wherein the modified timing threshold is adjusted to a value that is closer to a patient average breath rate or period if a spontaneous patient breath is absent during the breath cycle.

4. The apparatus according to claim 2, wherein the modified timing threshold is adjusted to a value that is further away from a patient average breath rate or period if a spontaneous patient breath is detected during the breath cycle.

5. The apparatus according to claim 1, wherein the adjustment of the initial timing threshold is based on a measure of adequacy of patient ventilation.

6. The apparatus according to claim 5, wherein the ventilation generation device is set to deliver a target ventilation and the sensor is configured to measure actual ventilation and the adequacy of patient ventilation comprises a relationship between the target ventilation and the actual measured ventilation.

7. The apparatus according to claim 6, wherein the relationship comprises a ratio of the actual measured ventilation and the target ventilation.

8. The apparatus according to claim 6, wherein the sensor comprises a flow sensor or a differential pressure transducer and the actual measured ventilation is determined from a signal from the flow sensor or the differential pressure transducer.

9. The apparatus according to claim 6, wherein the apparatus comprises a servoventilator.

10. The apparatus according to claim 9, wherein the ventilation generation device comprises an impeller and a motor.

11. A method for adjusting back-up ventilation support in a ventilator, the ventilator having a controller and the method comprising:
    initiating, with the controller, delivery of a first machine initiated breath if a spontaneous patient breath is not detected before lapsing of a first timing threshold;
    adjusting, by the controller, the first timing threshold to a second timing threshold based on a predetermined number of machine initiated breath counts; and
    initiating with the controller a second machine initiated breath as a function of the second timing threshold.

12. The method according to claim 11, wherein the predetermined number of machine initiated breath counts comprise a breath cycle.

13. The method according to claim 12, further comprising adjusting, by the controller, the first timing threshold so that the second timing threshold is closer to a patient average breath rate or period if the spontaneous patient breath is not detected before lapsing of the first timing threshold.

14. The method according to claim 12, further comprising adjusting, by the controller, the first timing threshold so that the second timing threshold is further away from a patient average breath rate or period if the spontaneous patient breath is not detected before lapsing of the first timing threshold.

15. The method according to claim 11, further comprising adjusting the first timing threshold to the second timing threshold based on a measure of adequacy of patient ventilation.

* * * * *